United States Patent [19]

Stürzebecher

[11] Patent Number: 6,087,119

[45] Date of Patent: Jul. 11, 2000

[54] METHOD FOR DETERMINING THE CATALYTIC ACTIVITY OF FACTOR IXA

[75] Inventor: Jörg Stürzebecher, Erfurt-Rhoda, Germany

[73] Assignee: Roche Diagnostics GmbH, Mannheim, Germany

[21] Appl. No.: 09/297,453

[22] PCT Filed: Oct. 15, 1997

[86] PCT No.: PCT/EP97/05660

§ 371 Date: Apr. 30, 1999

§ 102(e) Date: Apr. 30, 1999

[87] PCT Pub. No.: WO98/18957

PCT Pub. Date: May 7, 1998

[30] Foreign Application Priority Data

Oct. 31, 1996 [EP] European Pat. Off. ............. 96117470

[51] Int. Cl.[7] ............................ C12Q 1/56; G01N 33/50; C07K 5/08
[52] U.S. Cl. ................................. 435/13; 436/69; 530/331
[58] Field of Search ........................ 435/13, 212; 436/69, 436/131; 530/331; 930/21, 250

[56] References Cited

U.S. PATENT DOCUMENTS

| | | | |
|---|---|---|---|
| 4,480,030 | 10/1984 | Svendsen | 435/13 |
| 4,904,641 | 2/1990 | Eibl et al. | 514/2 |
| 5,399,487 | 3/1995 | Buténas et al. | 435/13 |
| 5,839,443 | 11/1998 | Rose et al. | 128/898 |

FOREIGN PATENT DOCUMENTS

| | | | |
|---|---|---|---|
| 0672659 | 3/1995 | European Pat. Off. | C07D 211/60 |
| WO 92/15324 | 9/1992 | WIPO | |
| WO 97/47737 | 12/1997 | WIPO | |

*Primary Examiner*—Ralph Gitomer
*Assistant Examiner*—Marjorie A. Moran
*Attorney, Agent, or Firm*—George W. Johnston; William H. Epstein; John P. Parise

[57] ABSTRACT

A method for the determination of factor IXa in a sample solution using a measurable factor IXa substrate and a water-miscible alcohol and measuring the cleavage of the factor IXa substrate as a measure for factor IXa activity is suitable for the direct determination of factor IXa.

33 Claims, 3 Drawing Sheets

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 1
aaaaaaccat ggttgttggt ggagaagatg ccaaacc                           37

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 2
aaaaaaaagc ttcattaagt gagctttgtt ttttccttaa tc                     42

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 3
aaaaaaccat ggatgtaaca tgtaacatta agaatggca                         39
```

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 4
gggttcgtcc agttccagaa gggc                                          24
```

METHOD FOR DETERMINING THE CATALYTIC ACTIVITY OF FACTOR IXA

This application is the US national phase of PCT/EP97/05660, filed Oct. 15, 1997.

The invention concerns a method for determining the catalytic activity of factor IXa. The method according to the invention is suitable for finding factor IXa inhibitors (screening), for modulating blood coagulation (therapeutic application) and for determining factor IX and factor IXa in body fluids (diagnostic application).

Blood plasma proteases play a role in blood coagulation, wound closure by fibrin formation as well as in fibrinolysis i.e. clot lysis. After an injury the "injury signal" is amplified by the sequential activation (specific proteolysis) of inactive proenzymes to form active enzymes which initiates blood coagulation and ensures a rapid wound closure. Blood coagulation can be initiated by two paths, the intrinsic path in which all protein components are present in the blood and the extrinsic path in which a membrane protein, the so-called tissue factor plays a critical role.

The molecular mechanism of blood homeostasis (blood coagulation, fibrinolysis and the regulation of this equilibrium) and the components that are involved in this are comprehensively described in several review articles (Furie, B. and Furie, B. C., Cell 53 (1988) 505–518; Davie, E. W. et al., Biochem. 30 (1991) 10363–10379; Bergmeyer, H. U. (ed.): Methods of Enzymatic Analysis, Vol. V, chapter 3, 3rd ed., Academic Press, New York (1983)).

The factors of the blood coagulation cascade are very complex proteins. As a rule they can only be isolated in a complicated manner from the natural raw material source, the blood plasma, in a limited amount, with varying quality, homogeneity and purity (Van Dam-Mieras, M.C.E. et al., In: Bergmeyer, H. U. (ed.), Methods of Enzymatic Analysis, Vol. V, 3rd ed., page 365–394, Academic Press, New York (1983)). They play an important role in the regulation of blood homeostasis which is the equilibrium between blood coagulation, clot formation and dissolution. This well-regulated system can become unbalanced by genetic defects such as haemophilia A (defective factor VIII) and haemophilia B (defective factor IX). Acute disorders can lead to cardiac infarction, embolism and stroke.

There is therefore a need for substances which can influence the system of blood coagulation and fibrinolysis according to the medical requirements. For example from blood isolated or recombinantly produced factor VIII or factor IX are used to treat haemophilia A and B. tPA (tissue type plasminogen activator) and streptokinase (bacterial plasminogen activator) are used for example for clot lysis e.g. after cardiac infarction. In addition to complex proteins, substances such as hirudin (peptide composed of 65 amino acids, thrombin inhibitor), heparin (heteroglycan, cofactor of endogenous inhibitors) and vitamin K antagonists (inhibitors of γ-carboxylation of Glu residues of the GlA domain) are also used to inhibit blood coagulation. However, the available substances are often still very expensive (protein factors) and not ideal with regard to their medical application (side effects) so that there is a need for medicaments which can be used to specifically modulate blood coagulation and clot lysis.

The search for new modulators (activators, inhibitors) of blood coagulation, fibrinolysis and homeostasis can for example be carried out by screening substance libraries and subsequently improving an identified lead structure by drug modelling. For this it is necessary that i) a suitable test and ii) the key protein(s) [target(s)] are available in an adequate amount and quality for screening and for crystal structure investigations (e.g. improvement of the lead structure by the specific prediction of changes based on the 3D structure of the protein component and lead structure).

Factor IXa (FIXa) is an interesting target for an inhibitor screening in order to find inhibitors to modulate blood coagulation. The known clinical picture of haemophilia B (factor IXa defect) warrants the assumption that specific factor IXa inhibitors are superior to known thrombin inhibitors with regard to the quite considerable pleiotropic side-effects.

Previously, screening for FIXa inhibitor activity has failed due to the availability and extremely low catalytic activity of FIXa.

The isolation of the inactive serine protease FIX (zymogen) from blood plasma and the subsequent activation by proteolysis is difficult, time-consuming, expensive and often does not yield the desired amount and quality. Thus the plasma concentration of the inactive protease zymogen FIX is only 0.5 mg/l (Furie, B. and Furie B. C., Cell 53 (1988) 505–518). Moreover the protease preparations isolated from the plasma and activated in vitro are often very heterogeneous and unstable.

The inactive FIX zymogen can for example be activated/converted using purified FXIa (Van Dam-Mieras, M.C.E.; Muller, A. D.; van Dieijen, G.; Hemker, H. C.: Blood coagulation factors II, V, VII, VIII, IX, X and XI: Determination with synthetic substrates. In: Bergmeyer, H. U. (ed.): Methods of Enzymatic Analysis, Vol. V, Enzymes 3: Peptidases, Proteinases and Their Inhibitors, page 365–394, 3rd ed., Academic Press, New York (1983)).

Blood plasma proteases are complex glycoproteins that belong to the serine protease family. They are synthesized in the liver as inactive proenzymes (zymogens), secreted into the blood and are activated when required by specific proteolysis i.e. by cleavage of one or two peptide bonds. They are structurally very similar with regard to the arrangement of their protein domains and their composition (Furie, B. and Furie, B. C., Cell 53 (1988) 505–518).

According to Furie B. and Furie, B. C. the proteases of the factor IX family (factor VII, IX, X and protein C) are composed of
  a propeptide,
  a GLA domain,
  an aromatic amino acid stack domain,
  two EGF domains (EGF1 and EGF2),
  a zymogen activation domain (activation peptide, AP) and
  a catalytic protease domain (CD).

Furthermore the blood plasma proteases are post-translationally modified during secretion:
  11–12 disulfide bridges
  N- and/or O-glycosylation (GLA domain and activation peptide)
    Bharadwaj, D. et al., J. Biol. Chem. 270 (1995) 6537–6542
    Medved, L. V. et al., J. Biol. Chem. 270 (1995) 13652–13659
  cleavage of the propeptide
  γ-carboxylation of Glu residues (GLA domain)
  β-hydroxylation of an Asp residue (EGF domains)
  cleavage of the zymogen region (partially)

After activation of the zymogens (zymogenic form of the protein) by specific cleavage of one or two peptide bonds (cleavage of an activation peptide), the enzymatically active proteases are composed of two chains which, in accordance with their molecular weight, are referred to as the heavy and light chain. In the factor IX protease family the two chains are held together by an intermolecular disulfide bridge between the EGF2 domain and the protease domain. The zymogen-enzyme transformation (activation) leads to conformation changes within the protease domain. This enables an essential salt bridge necessary for the protease activity to form between the N-terminal amino acid of the protease domain and an Asp residue within the protease domain. The N-terminal region is very critical for this subgroup of serine proteases and should not be modified. Only then is it possible for the typical active site of the serine proteases to form with the catalytic triad composed of Ser, Asp and His [Blow, D. M.: Acc. Chem. Res. 9 (1976) 145–152; Polgar, L.: In: Mechanisms of protease action. Boca Raton, Fla., CRC Press, chapter 3 (1989)].

Blood plasma proteases can be produced in a classical manner by isolating the inactive zymogens from the blood and subsequently activating them or they can be produced recombinantly by expressing the corresponding cDNA in a suitable mammalian cell line or in yeast.

The production of coagulation factors by expression/secretion of the zymogens or active proteases by means of eukaryotic host/vector systems is described for FvII: Hagen, F. S. et al., EP 0 200 421; Pedersen, A. H. et al., Biochem. 28 (1989) 9391–9336; FIX: Lin, S.-W. et al., J. Biol. Chem. 265 (1990) 144–150; FX: Wolf, D. L. et al., J. Biol. Chem. 266 (1991) 13726–13730, Protein C: Bang, N. U. et al., EP 0 191 606.

As a rule host cells are used which are able to post-translationally modify the coagulation factors like the native enzyme during the secretion process. The zymogen-enzyme transformation is then carried out subsequently during the downstream processing e.g. by using an activator from snake venom in the case of prothrombin or factor X (Sheehan, J. P. et al., J. Biol. Chem. 268 (1993) 3639–3645; Fujikawa, K. et al. Biochem. 11 (1972) 4892–4898).

For the purpose of zymogen-enzyme activation in vivo (already during secretion), the natural zymogen cleavage sites or the entire activation peptide were substituted by protease cleavage sites (several adjacent basic amino acids) which can be cleaved by specifically cleaving proteases that occur naturally in the secretion path of the host cell such as e.g. Kex2 (yeast) or PACE (mammnalian cell lines). (FX: Wolf, D. L. et al., J. Biol. Chem. 266 (1991) 13726–13730; Prothrombin: Holly, R. D. and Foster, D. C., WO 93/13208).

The production of variants of coagulation factors (FX: Rezaie, A. R: et al., J. Biol. Chem. 268 (1993) 8176–8180); FIX: Zhong, D. G. et al., Proc. Natl. Acad. Sci. USA 91 (1994) 3574–3578), mutants (FX: Rezaie, A. R. et al., J. Biol. Chem. 269 (1994) 21495–21499; Thrombin: Yee, J. et al., J. Biol. Chem. 269 (1994) 17965–17970); FVII: Nicolaisen, E. M. et al., WO 88/10295) and chimeras e.g. composed as FIX and FX (Lin, S.-W. et al., J. Biol. Chem. 265 (1990) 144–150; Hertzberg, M. S. et al., J Biol. Chem. 267 (1992) 14759–14766) by means of eukaryotic host/vector systems is also known.

However, expression in eukaryotic mammalian cell lines is time-consuming, limited with regard to expression output and expensive. In addition undesired post-translational modifications can occur.

The production of blood plasma proteases by expression in prokaryotes and subsequent renaturation of the expression product is described by Thogersen, H. C. et al. (WO 94/18227). According to this FX variants are renatured by means of a cyclic renaturation process in which the inactive FX protein is immobilized in a chromatographic column by means of a metal chelate complex (poly(His)-affinity handle). A fusion protein is used for this composed of a truncated FX variant (EGF1, EGF2 and protease domain), an additional FXa protease recognition sequence and an attachment aid at the C-terminus of the catalytic domain composed of 6 histidine residues.

Surprisingly it was found that the catalytic activity of factor IXa with respect to substrates can be stimulated by alcohols and hence a very sensitive factor IXa test can be constructed in a simple manner.

Consequently the invention concerns a method for determining factor IXa in a sample solution characterized in that a determinable factor IXa substrate and an alcohol that is homogeneously miscible with water and forms one phase is added to the sample solution and the cleavage of the factor IXa substrate is determined as a measure for the factor IXa activity. It surprisingly turned out that the catalytic factor IXa activity can be increased by more than 20 times by alcohols. As a result it is possible to directly determine the factor IXa activity in sample solutions. Factor IX can for example be determined in sample solutions, preferably body fluids such as plasma after activating factor IX to factor IXa by means of Russels viper venom or by the protease isolated from the snake venom (RVV-X protease).

A further subject matter of the invention is the use of the determination method according to the invention for factor IXa to screen for substances which modulate (inhibit or activate) factor IXa activity. Consequently the invention concerns a method for identifying a substance which modulates the activity of factor IXa characterized in that a) a factor IXa substrate is cleaved by a polypeptide with factor IXa activity at a defined concentration in the presence of an alcohol and the rate of cleavage of the said substrate is determined as a measure for the factor IXa activity, b) the said activity is measured in the presence of a test substance, c) the activity is compared with and without the test substance and d) the difference of the activity is used as a measure for the activity modulation by the test substance.

The inhibition of factor IXa by a test substance is preferably tested.

Suitable factor IXa substrates are for example factor IXa substrates that are described in EP-B 0 034 122. Substrates of the R-Xxx-Gly-Arg-pNA type are especially suitable in which Xxx represents a hydrophobic D-amino acid and pNA represents a determinable leaving group. R is defined analogously to EP-B 0 034 122. Substrates of the general formula I from EP-B 0 034 122 in which $R^3=R^4=H$ are preferred.

Preferred substrates are tripeptides with a hydrophobic D-amino acid at the N-terminus and preferably a cyclohexyl-substituted hydrophobic D-amino acid is used. Cyclohexyl-glycine and cyclohexylalanine are particularly preferred.

Further preferred substrates are for example substrates which are also cleaved by factor Xa such as e.g. Chromozym X (Boehringer Mannheim GmbH, Moc-D-Nle-Gly-Arg-pNA) or Pefachrom tPA (Pentapharm Ltd., Basel, $MeSO_2$-D-HHT-Gly-Arg-pNA). Commercial (preferably chromogenic or fluorogenic) substrates that can be determined optically are preferably used. The latter are chromogenic peptides/substrates with a cleavable residue that can be easily determined by optical means (the p-nitroaniline residue is preferred). The method according to the invention is preferably carried out in a buffer solution. All buffers that are effective in a pH range of 7–10 (preferably between pH 7.5–9.0) can be used as buffer substances. Tris buffer, triethanolamine and Tris-imidazole buffer are preferred.

The determination of FIXa activity and the screening assay are preferably carried out at 20–40° C., particularly preferably at room temperature and the amount of the cleaved optically determinable group is determined photometrically or fluorometrically. The absorbance at 405 nm is preferably determined. The enzymatic activity and the kinetic constants are determined from the linear initial slope according to the Michaelis-Menten equation.

Factor IX or the ratio of factor IX to factor IXa can be determined analogously after activation of factor IX to factor IXa. In order to determine factor IX in plasma, factor IX is firstly activated to factor IXa by Russels viper venom (preferably 0.2 mg/ml) or RVV-X protease (preferably 0.1 mg/ml) in the presence of $CaCl_2$ (10 mmol/l) at 20–40° C., preferably at 37° C. After the activation is completed (preferably 15 min), ethylene glycol and the cleavable substrate are added at concentrations of 20–40% and 0.2–1 mmol/l respectively.

It has proven to be advantageous for a screening test to add factor IXa at a concentration of 0.02–0.5 μmol/l, preferably 0.05 μmol/l and the cleavage substrate at a concentration of 0.2–1 mmol/l with a test substance concentration in the μmol/l range. Ethylene glycol, ethanol or methanol is preferably used as the alcohol. The concentration of the alcohol is preferably in the range of 20–40%. Native human factor IXa or porcine or bovine factor IXa or recombinantly produced human factor IXa can be used as factor IXa. A truncated human recombinant factor IXa that is described in EP 96 109 288.9 is particularly preferably used.

Enzymatically active recombinant factor IXa can be produced by expression of a corresponding DNA in prokaryotes, renaturation of the expression product and enzymatic cleavage if it is composed of a FIXa serine protease domain (catalytic domain) N-terminally linked to an EGF domain (EGF1 and/or EGF2) and a zymogen activation domain.

A non-glycosylated, enzymatically active factor IXa composed of the following domains is preferably used:

a) the catalytic FIXa protease domain, N-terminally linked with b) a zymogen activation domain, N-terminally linked with c) an EGF1 and/or EGF2 domain (preferably EGF2 or EGF1 and EGF2).

A spacer with up to 50 amino acids is preferably inserted between the zymogen activation domain and the EGF domain (or the EGF domains). When the zymogenic one chain form according to the invention is cleaved in the zymogen activation domain, an active protein is obtained in a two chain form. Both chains are linked by an intermolecular disulfide bridge in the two chain form. The proteins according to the invention are preferably composed of the EGF2 domain, the activation peptide and the catalytic domain of factor IX. Such factor IX muteins are described in the European Patent Application No. 96 110 959.2.

Any plasma can be used in the determination method according to the invention and citrate plasma is preferred.

The method can be carried out at neutral or weakly alkaline pH values preferably in the pH range between 7.5 and 9.0. Physiologically acceptable buffers that are effective in this range can be used as the buffer. In addition common stabilizers and preservatives for coagulation tests such as bovine serum albumin, merthiolate and such like can also be added.

In addition the method according to the invention and the reagent according to the invention can also contain a surfactant, preferably a non-ionic surfactant such as Tween 80®. In this case the concentration is preferably 0.01–1 vol. %.

A further subject matter of the invention is a reagent for the determination of factor IXa which contains an optically measurable substrate that can be cleaved by factor IXa, alcohol and buffer in a range between pH 7 and 10.

The following examples, publications, the sequence protocol and the figures further elucidate the invention, the protective scope of which results from the patent claims. The described methods are to be understood as examples which also still describe the subject matter of the invention even after modifications.

Methods

Recombinant DNA Technique

Figure 1:
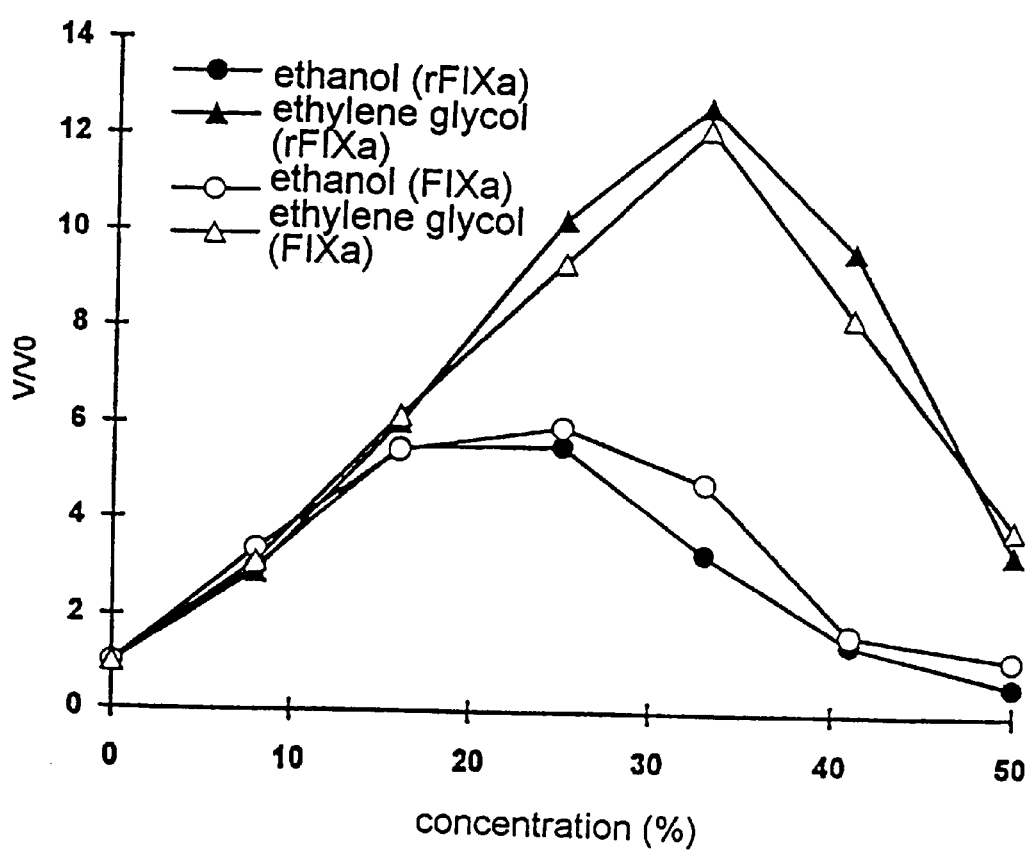
FIG. 1 shows the influence of ethanol and ethylene glycol on the activity of recombinant rFIXa (0.48 μmol/l) and native FIXa (0.14 μmol/l). pH 7.4; substrate: $MeSO_2$-D-HHT-Gly-Arg-pNA (1.02 mmol/l)—figure for table 2.

Standard methods were used to manipulate DNA as described in Sambrook, J. et al. (1989) In: Molecular cloning: A laboratory manual. Cold Spring Harbor Laboratory Press, Cold Spring Harbor, N.Y. The molecular biological reagents were used according to the manufacturer's instructions.

Protein Determination

The protein concentration of the FIX variants was determined by determining the optical density (OD) at 280 nm using the molar extinction coefficients calculated on the basis of the amino acid sequence.

Expression Vector

The vector for the expression of the FIX variants is based on the expression vector pSAM-CORE for core-streptavidin. The preparation and description of the plasmid PSAM-CORE is described in WO 93/09144.

The core-streptavidin gene was replaced by the gene of the desired variant in the PSAM-CORE vector.

EXAMPLE 1

Cloning the Catalytic Domain of the FIX Gene (Plasmid: pFIX-CD)

The FIX cDNA from bp position 690 to 1403, coding for the FIX protease domain from amino acid position 181 to 415 (cDNA sequence and amino acid sequence numbering according the publication of McGraw, R. A. et al. (Proc. Natl. Acad. Sci. USA 82 (1985) 2847–2851) was amplified using the PCR primers N1 (SEQ ID NO:1) and N2 (SEQ ID NO:2).

```
                NcoI
N1: 5'-AAAAAACCATGGTTGTTGGTGGAGAAGATGCCAAACC-3'
              MetValValGlyGlyGluAspAlaLys

HindIII
N2: 5'-AAAAAA
AAGCTTCATTAAGTGAGCTTTGTTTTTTCCTTAATC-3'
``` and a commercially available human liver cDNA gene bank (vector: Lambda ZAP® II) from the Stratagene Company (La Jolla, Calif., U.S.A.) as template DNA. The PCR primers introduced a singular NcoI cleavage site and an ATG start codon at the 5' end of the coding region and a singular HindIII cleavage site at the 3' end of the coding region.

The ca. 730 bp long PCR product was digested with the restriction endonucleases NcoI and HindIII and the ca. 720 bp long NcoI/HindIII-FIX fragment was ligated into the ca. 2.55 kbp long NcoI/HindIII-pSAM-CORE vector fragment (see WO 93/09144) after purification by agarose gel electrophoresis. The desired plasmid pFIX-CD was identified by restriction mapping and the FIX cDNA sequence isolated by PCR was checked by DNA sequencing.

EXAMPLE 2
Construction of the FIX Protease Gene with EGF2 Domain, activation peptide and catalytic domain (plasmid: pFIX-EGF2-AP-CD)

The FIX cDNA from bp position 402 to 986, coding for the EGF2 domain, the activation peptide and the N-terminal region of the FIXa protease domain from amino acid position 85 to 278 (McGraw et al. Proc. Natl. Acad. Sci. USA 82 (1985) 2847–2851) was amplified using the PCR primers N3 (SEQ ID NO:3) and N4 (SEQ ID NO:4).

```
               NcoI
N3: 5'-AAAAAACCATGGATGTAACATGTAACATTAAGAATGGCA-3'
              MetAspValThrCysAsnIleLysAsnGly

N4: 5'-GGGTTCGTCCAGTTCCAGAAGGGC-3'
``` and a commercially available human liver CDNA gene bank (vector: Lambda ZAP® II) from the Stratagene Company (La Jolla, Calif., U.S.A.) as template DNA. The PCR primer N3 introduced an ATG start codon and a singular NcoI cleavage site at the 5' end of the coding region.

The ca. 590 bp long PCR product was digested with the restriction endonucleases NcoI and BsmI and the ca. 360 bp long NcoI/BsmI-FIX-EGF2-AP fragment was ligated into the ca. 3.2 kbp long NcoI/BsmI-pFIX-CD vector fragment (example 1) after purification by agarose gel electrophoresis. The desired plasmid pFIX-EGF2-AP-CD was identified by restriction mapping and the FIX cDNA sequence isolated by PCR was checked by DNA sequencing.

EXAMPLE 3
a) Expression of the FIXa Protease Gene in *E. coli*

In order to express the FIX gene containing the activation peptide, the *E. coli* K12 strain UT5600 (Grodberg, J. and Dunn, J. J. J. Bacteriol. 170 (1988) 1245–1253) was transformed with the expression plasmid pFIX-EGF2-AP-CD (ampicillin resistance) described in example 2 and with the lacI$^q$ repressor plasmid pUBS520 (kanamycin resistance, preparation and description see: Brinkmann, U. et al., Gene 85 (1989) 109–114). Other *E. coli* strains known and available to a person skilled in the art such as HB101 and *E. coli* B can also be used instead of the strain UT5600.

The UT5600/pUBS520 cells transformed with the expression plasmid pFIX-EGF2-AP-CD were cultured in a shaking culture in DYT medium (1% (w/v) yeast extract, 1% (w/v) Bacto Tryptone, Difco and 0.5% NaCl) containing 50–100 mg/l ampicillin and 50 mg/l kanamycin at 37° C. up to an optical density at 550 nm ($OD_{550}$) of 0.6–0.9 and subsequently induced with IPTG (final concentration 1–5 mmol/l). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer pH 7.2 and stored at −20° C. until further processing. The cell yield from a 1 l shaking culture was 4–5 g (wet weight).

b) Expression Analysis

The expression of the UT5600/pUBS520 cells transformed with the plasmid pFIX-EGF2-AP-CD was analysed. For this purpose cell pellets from in each case 1 ml centrifuged culture medium were resuspended in 0.25 ml 10 mmol/l Tris-HCl, pH 7.2 and the cells were lysed by ultrasonic treatment (2 pulses of 30 s at 50% intensity) using a Sonifier® Cell Disruptor B15 from the Branson Company (Heusenstamm, Germany). The insoluble cell components were sedimented (Eppendorf 5415 centrifuge, 14000 rpm, 5 min) and ⅕ volumes (vol) 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction (pellet) was resuspended in 0.3 ml 1×SDS sample buffer containing 6–8 M urea, the samples were incubated for 5 min at 95° C. and centrifuged again. Afterwards the proteins were separated by SDS polyacrylamide gel electrophoresis (PAGE) (Laemmli, U.K., Nature 227 (1970) 680–685) and stained with Coomassie Brilliant Blue R dye.

The FIX variant synthesized in *E. coli* was homogeneous and was exclusively found in the insoluble cell debris fraction (inclusion bodies, IBs). The expression yield was 10–50% relative to the total *E. coli* protein.

EXAMPLE 4
Cell Lysis, Solubilization and Renaturation
a) Cell Lysis and Preparation of Inclusion Bodies (IBs)

The cell pellet from 3 l shaking culture (ca. 15 g wet weight) was resuspended in 75 ml 50 mmol/l Tris-HCl, pH 7.2. The suspension was admixed with 0.25 mg/ml lysozyme and it was incubated for 30 min at 0° C. After addition of 2 mmol/l $MgCl_2$ and 10 μg/ml DNase I (Boehringer Mannhein GmbH, catalogue No. 104159) the cells were disrupted mechanically by means of high pressure dispersion in a French® Press from the SLM Amico Company (Urbana, Ill., USA). Subsequently the DNA was digested for 30 min at room temperature (RT). 37.5 ml 50 mmol/l Tris-HCl pH 7.2, 60 mmol/l EDTA, 1.5 mol/l NaCl, 6% Triton X-100 was added to the preparation, it was incubated for a further 30 min at RT and centrifuged in a Sorvall RC-5B centrifuge (GSA Rotor, 12000 rpm, 15 min). The supernatant was discarded, 100 ml 50 mmol/l Tris-HCl, pH 7.2, 20 mmol/l EDTA was added to the pellet, it was incubated for 30 min while stirring at 4° C. and again sedimented. The last wash step was repeated. The purified IBs (1.5–2.0 g wet weight, 25–30% dry mass, 100–150 mg protease) were stored at −20° C. until further processing.

b) Solubilization and Derivatization of the IBs

The purified IBs were suspended within 1 to 3 hours at room temperature while stirring at a concentration of 100 mg IB pellet (wet weight)/ml corresponding to 5–10 mg/ml protein in 6 mol/l guanidinium-HCl, 100 mmol/l Tris-HCl, 20 mmol/l EDTA, 150 mmol/l GSSG and 15 mmol/l GSH, pH 8.0. Afterwards the pH was adjusted to pH 5.0 and the insoluble components were separated by centrifugation (Sorvall RC-5B centrifuge, SS34 rotor, 16000 rpm, 10 min). The supernatant was dialysed for 24 hours at 4° C. against 100 vol. 4–6 mol/l guanidinium-HCl pH 5.0.

c) Renaturation

The renaturation of the proteins solubilized in 6 mol/l guanidinium-HCl and derivatized with GSSG/GSH was carried out at 4° C. by repeated (e.g. 3-fold) addition of 0.5 ml IB solubilisate/derivative in each case to 50 ml 50 mmol/l Tris-HCl, 0.5 mol/l arginine, 20 mmol/l $CaCl_2$, 1 mmol/l EDTA and 0.5 mmol/l cysteine (pH 8.5) at intervals of 24 hours and subsequent incubation for 48 hours at 4° C. After completion of the renaturation reaction the insoluble components were separated by filtration with a filtration apparatus from the Satorius Company (Gottingen, Germany) equipped with a deep bed filter K 250 from the Seitz Company (Bad Kreuznach, Germany).

d) Concentration and Dialysis of the Renaturation Preparations

The clear supernatant containing protease was concentrated 10–15-fold by cross-flow filtration in a Minisette (membrane type: Omega 10K) from the Filtron Company (Karlstein, Germany) and dialysed for 24 hours at 4° C. against 100 volumes 20 mmol/l Tris-HCl and 50 mmol/l NaCl, pH 7.2 to remove guanidinium-HCl and arginine. Precipitated protein was removed by centrifugation (Sorvall RC-5B centrifuge, SS34 rotor, 16000 rpm, 20 min) and the clear supernatant was filtered with a Nalgene® disposable filtration unit (pore diameter: 0.2 $\mu$m) from the Nalge Company (Rochester, N.Y., USA).

EXAMPLE 5

Purification of the Renatured FIX Variant

The FIX variant from the renaturation preparation can, if required, be further purified with chromatographic methods which are known to a person skilled in the art.

a) Purification of the FIX Variant by Ion Exchange Chromatography on Q-Sepharose-ff The concentrated renaturation preparation that had been dialysed against 20 mmol/l Tris-HCl and 50 mmol/l NaCl, pH 8.0 was applied to a Q-Sepharose ff column (1.5×11 cm, V=20 ml; loading capacity: 10 mg protein/ml gel) from the Pharmacia Biotech Company (Freiburg, Germany) (2 column volumes/hour, 2 CV/h) equilibrated with the same buffer and it was washed with the equilibration buffer until the absorbance of the eluate at 280 nm had reached the blank value of the buffer. The bound material was eluted by a gradient of 50–500 mmol/l NaCl in 20 mmol/l Tris-HCl, pH 8.0 (2 CV/ h). The FIX variant was eluted at an NaCl concentration of 100–150 mmol/l. The fractions containing FIX were identified by non-reducing and reducing SDS PAGE and the elution peak was pooled.

b) Final Purification of the FIX Variant by Ion Exchange Chromatography on Heparin-Sepharose CL-6B After chromatography on Q-Sepharose ff, the combined fractions containing FIX were directly applied (2 CV/h) to a heparin-Sepharose CL-6B column (1.5×11 cm, V=20 ml, loading capacity: 1 mg protein/ml gel) from the Pharmacia Biotech Company (Freiburg, Germany) that had been equilibrated with 20 mmol/l Tris-HCl and 200 mmol/l NaCl, pH 8.0. Afterwards it was washed with equilibration buffer until the absorbance of the eluate at 280 nm reached the blank value for the buffer. The bound material was eluted by a gradient of 0.2–1.0 mol/l NaCl in 20 mmol/l Tris-HCl, pH 8.0 (2 CV/h). The FIX variants were eluted at an NaCl concentration of 500–600 mmol/l. The fractions containing FIX were identified by non-reducing and reducing SDS PAGE, the elution peak was combined and dialysed against 20 mmol/l Tris-HCl, 50–200 mmol/l NaCl, 5 mmol/l $CaCl_2$, pH 7.8.

EXAMPLE 6

Activation and Purification of the FIX Variant

The renatured purified FIX variant was activated with purified Russells viper venom (RVV-X) protease. The RVV-X protease was, as described in the publication by Esmon, C. T. (prothrombin activation, doctoral dissertation, Washington University, St. Louis, Mo. (1973)), purified from the commercially available snake venom lyophilisate from Sigma Aldrich Chemie GmbH Co. (Deisenhofen, Germany) by gel filtration followed by ion exchange chromatography on Q-Sepharose ff .

a) Activation and Purification of the Renatured FIX Variant

The FIX variant was digested at 25° C. at a concentration of 0.5 to 2.0 mg/ml and a protease/substrate ratio of 1:10 to 1:20 in 20 mmol/l Tris-HCl, 50 mmol/l NaCl, 10 mmol/l $CaCl_2$, pH 7.8. The time course of the enzymatic FIX activation was monitored by determining the activity with a chromogenic substrate (see example 13a) until the digestion was completed (plateau, maximum activation). For this purpose samples (10 to 100 $\mu$l) were taken from the reaction mixture at intervals of 3–4 h over a period of up to 24 hours and the generated FIXa activity was determined. After reaching the activation plateau, the activation preparation was purified by negative chromatography on Q-Sepharose-ff.

RVV-X and the non-activated FIX variant bind under the given conditions to Q-Sepharose-ff, but the activated FIXa variant does not.

The activation preparation was applied (2 CV/h) to a Q-Sepharose-ff column (1.0×10 cm, V=8 ml) from the Pharmacia Biotech Company (Freiburg, Germany) which had been equilibrated with 20 mmol/l Tris-HCl, 50 mmol/l NaCl, pH 7.8 and the column was developed with equilibration buffer while fractionating. The fractions containing protease were identified by non-reducing and reducing SDS PAGE and activity determination.

EXAMPLE 7

Characterization of the Purified Protease Variants a) Activity Test

The activity of the FIXa variants was determined using the chromogenic substrate Chromozym X (Boehringer Mannheim GmbH, Mannheim, Germany, cat. No. 789763). 10–100 $\mu$l sample was made up to 200 $\mu$l with 190–100 $\mu$l 50 mmol/l Tris-HCl, 150 mmol/l NaCl, 5 mmol/l $CaCl_2$, 0.1% PEG 8000, pH 8.0, admixed with 20 $\mu$l Chromozym X (0.5–40 mmol) and measured at a wavelength of 405 nm and RT against a reagent blank value in an ELISA reader. The activity and the kinetic constants were determined from the linear initial slope according to the Michaelis Menten equation.

b) SDS PAGE

Oligomer and aggregate formation by intermolecular disulfide bridge formation as well as the homogeneity and purity of the renatured activated and purified FIXa protease variant were examined by non-reducing (minus mercaptoethanol) and reducing (plus mercaptoethanol) SDS PAGE (Laemmli, UK, Nature 227 (1970) 680–685).

EXAMPLE 8

Factor IXa Test

The FIXa test was carried out with recombinantly produced native human FIXa as a sample and the peptide substrate $MeSO_2$-D-HHT-Gly-Arg-pNA (Pefachrom tPA, Pentapharm Ltd., Basel, Switzerland) or other chromogenic/fluorogenic substrates of the R-D-Xxx-Gly-Arg-pNA type (EP-B 0 034 122) in Tris-HCl buffer and the substances to be tested (alcohol, solvents and inhibitors). The reaction was started by adding FIXa.

Test Principle

FIXa

MeSO$_2$-D-HHT-Gly-Arg-pNA→MeSO$_2$-D-HHT-Gly-Arg+pNA measurement signal: pNA

FIXa substrates: MOC-D-Nle-Gly-Arg-pNA (Chromozym X)
MeSO$_2$-D-HHT -Gly-Arg -pNA (Pefachrom tPA)
MeSO$_2$-D-CHG-Gly-Arg-pNA
MeSO$_2$-D-CHA-Gly-Arg-pNA
MeSO$_2$-D-CHA-Gly-Arg-AMC Abbreviations: pNA, p-nitroaniline
AMC, 7-amino-4-methyl-coumaryl
MOC, methyloxycarbonyl
HHT, hexahydrotyrosine
CHG, cyclohexylglycine
CHA, cyclohexylalanine General Test Mixture 200 µl buffer 50–100 mmol/l Tris-HCl, pH 7–9.5

100–200 mmol/l NaCl 5 mmol/l CaCl$_2$ with additives (alcohols, solvents and inhibitors)
+25 µl peptide substrate (1–20 mmol/l)
+20 µl FIXa (0.02–0.5 4 µmol/l)

The test mixture was incubated at room temperature (25° C.) in a microtitre plate and the change in absorbance (ΔA/min) was measured at 405 nm using an ELISA reader. The activity and the kinetic constants were determined from the linear initial slope according to the Michaelis-Menten equation.

EXAMPLE 9

Influence of Alcohols and Organic Solvents on the Activity of rFIXa

The influence of various alcohols that can be completely mixed with water to form a single phase (methanol, ethanol, n-propanol, i-propanol, t-butanol, ethylene glycol and glycerol) and organic solvents [acetonitrile, DMSO (dimethylsulfoxide) and DMF (dimethylformamide) and readily soluble multivalent alcohols (m-erythritol, PEG (polyethylene glycol)] on the activity of rFIXa was examined in relation to the concentration of the alcohols or organic solvents (0–50%).

Test Mixture (Concentration in the Test)

41 mmol/l Tris-HCl, pH 7.4

82 mmol/l NaCl 4.1 mmol/ CaCl$_2$ 1.02 mmol/l MeSO$_2$-D-HHT-Gly-Arg-pNA 0.48 µmol/l rFIXa (human)

0–50% (alcohol or organic solvent)

The results are shown in table 1. The ratio V/V$_0$ was calculated to illustrate the stimulation of the catalytic activity of rFIXa.

V$_0$, reaction rate without additives

V, reaction rate in the presence of additives

TABLE 1

| Additive [%] | V/V$_0$ | | | | | |
|---|---|---|---|---|---|---|
| | 0 | 8 | 16 | 25 | 33 | 41 | 50 |
| Methanol | 1 | 2.16 | 3.46 | 3.71 | 2.83 | 1.55 | 0.588 |
| Ethanol | 1 | 2.99 | 5.52 | 5.57 | 3.35 | 1.48 | 0.606 |
| n-Propanol | 1 | 3.43 | 2.26 | 0.339 | 0.186 | 0.056 | 0.056 |
| i-Propanol | 1 | 2.17 | 2.48 | 1.18 | 0.346 | 0.164 | 0.164 |
| t-Butanol | 1 | 2.05 | 1.67 | 0.702 | 0.368 | 0.263 | 0.263 |
| Ethylene glycol | 1 | 2.91 | 6.05 | 10.27 | 12.68 | 9.68 | 3.41 |
| Glycerol | 1 | 1.12 | 1.64 | 2.47 | 3.38 | 4.82 | 5.91 |
| m-Erythritol* | 1 | 1.16 | 1.35 | 1.49 | 1.56 | 1.64 | 1.77 |
| PEG* | 1 | 0.691 | 0.410 | 0.352 | 0.309 | 0.216 | 0.173 |
| Acetonitrile | 1 | 0.828 | 0.314 | 0 | 0 | 0 | 0 |
| DMSO | 1 | 1.27 | 1.45 | 1.59 | 1.43 | 0.922 | 0.157 |
| DMF | 1 | 0.649 | 0.514 | 0 | 0 | 0 | 0 |

*g/100 ml

Result

The activity of rFIXa is stimulated ca. 5–15-fold by some alcohols (ethylene glycol>ethanol>methanol) in the concentration range of 15–40%. Glycerol does not stimulate until higher concentrations (25–50%) whereas m-erythritol only has a slight effect. In contrast polyethylene glycol (PEG) inhibits the activity of rFIXa. Of the solvents which contain no OH group only dimethylsulfoxide (DMSO) does not inhibit rFIXa up to 30% whereas dimethylformamide (DMF) and acetonitrile inactivate the enzyme.

EXAMPLE 10

Influence of Ethanol and Ethylene Glycol on the Activity of Recombinant Human FIXa and Native FIXa It was examined whether the observed stimulation of rFIXa (active rFXa variant composed of an EGFII domain, processed activation peptide and catalytic domain) by ethanol and ethylene glycol also occurs with native FIXa (human).

Test Mixture (Concentration in the Test)

41 mmol/l Tris-HCl, pH 7.4

82 mmol/l NaCl 4.1 mmol/l CaCl$_2$ 1.02 mmol/l MeSO$_2$-D-HHT-Gly-Arg-pNA 0.48 µmol/l human rFIXa or 0.14 µmol/l native FIXa (human)

0–50% ethanol or ethylene glycol

The results are summarized in table 2 and shown in FIG. 1.

TABLE 2

| Additive [%] | V/V$_0$ | | | | | |
|---|---|---|---|---|---|---|
| | 0 | 8 | 16 | 25 | 33 | 41 | 50 |
| Human rFIXa | | | | | | | |
| ethanol | 1 | 2.99 | 5.52 | 5.57 | 3.35 | 1.48 | 0.61 |
| ethylene glycol | 1 | 2.91 | 6.05 | 10.27 | 12.68 | 9.68 | 3.41 |
| Native FIXa (human) | | | | | | | |
| ethanol | 1 | 3.40 | 5.46 | 5.96 | 4.82 | 1.69 | 1.17 |
| ethylene glycol | 1 | 3.13 | 6.19 | 9.36 | 12.21 | 8.29 | 3.92 |

Result

No differences were found for recombinant human rFIXa and native human FIXa with regard to activation by ethanol and ethylene glycol.

EXAMPLE 11

Influence of Ethanol and Ethylene Glycol on the Activity of rFIXa Towards Chromogenic and Fluorogenic Peptide Substrates The stimulation of human rFIXa by ethanol and ethylene glycol was examined using the peptide substrates MeSO$_2$-D-HHT-Gly-Arg-pNA (Pefachrom tPA, Pentapharm Ltd., Basel, Switzerland), MOC-D-Nle-Gly-Arg-pNA (Chromozym X, Boehringer Mannheim GmbH, Mannheim, Germany, Cat.No. 789763), MeSO$_2$-D-CHG-Gly-Arg-pNA (Pentapharm Ltd., Basel, Switzerland), MeSO$_2$-D-CHA-Gly-Arg-pNA (Pentapharm Ltd., Basel, Switzerland) and MeSO$_2$-D-CHA-Gly-Arg-AMC (Pentapharm Ltd., Basel, Switzerland).

Test Mixture Chromogenic (Concentration in the Test)

42 mmol/l Tris-HCl, pH 7.4
82 mmol/l NaCl
4.1 mmol/l CaCl$_2$
0–50% ethylene glycol
1.02 mmol/l MeSO$_2$-D-HHT-Gly-Arg-pNA,
0.48 μmol/l rFIXa (human)

or 0.82 mmol/l MOC-D-Nle-Gly-Arg-pNA
0.48 μmol/l rFIXa (human)

or 1.02 mmol/l MeSO$_2$-D-CHG-Gly-Arg-pNA
0.28 μmol/l rFIXa (human)

or 1.02 mmol/l MeSO$_2$-D-CHA-Gly-Arg-pNA
0.48 μmol/l rFIXa (human)

Test Mixture Fluorogenic (Concentration in the Test)

42 mmol/l Tris-HCl, pH 7.4
82 mmol/l NaCl
4.1 mmol/l CaCl$_2$
0–50% ethylene glycol
0.51 mmol/l MeSO$_2$-D-CHA-Gly-Arg-AMC
0.08 μmol/l rFIXa (human)

Figure 2A:
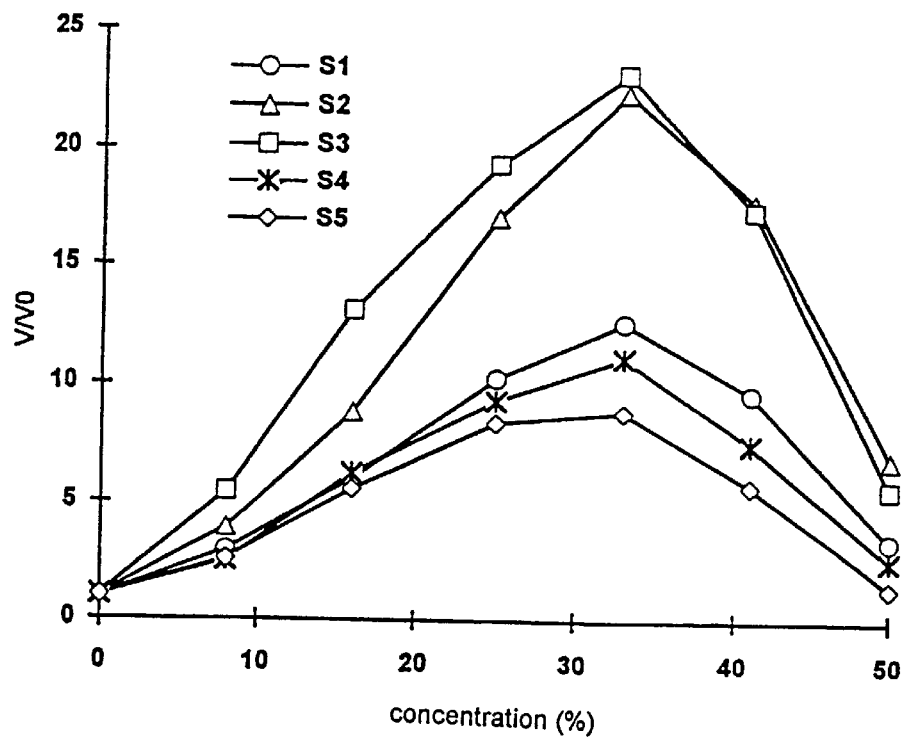
FIG. 2a shows the influence of ethylene glycol on the activity of rFIXa. S1=$MeSO_2$-D-HHT-Gly-Arg-pNA; S2=MOC-D-Nle-Gly-Arg-pNA; S3=$MeSO_2$-D-CHG-Gly-Arg-pNA; S4=$MeSO_2$-D-CHA-Gly-Arg-pNA; S5=$MeSO_2$-D-CHA-Gly-Arg-AMC; rFIXa=0.48 μmol/l; pH=7.4—figure for table 3.
Figure 2B:
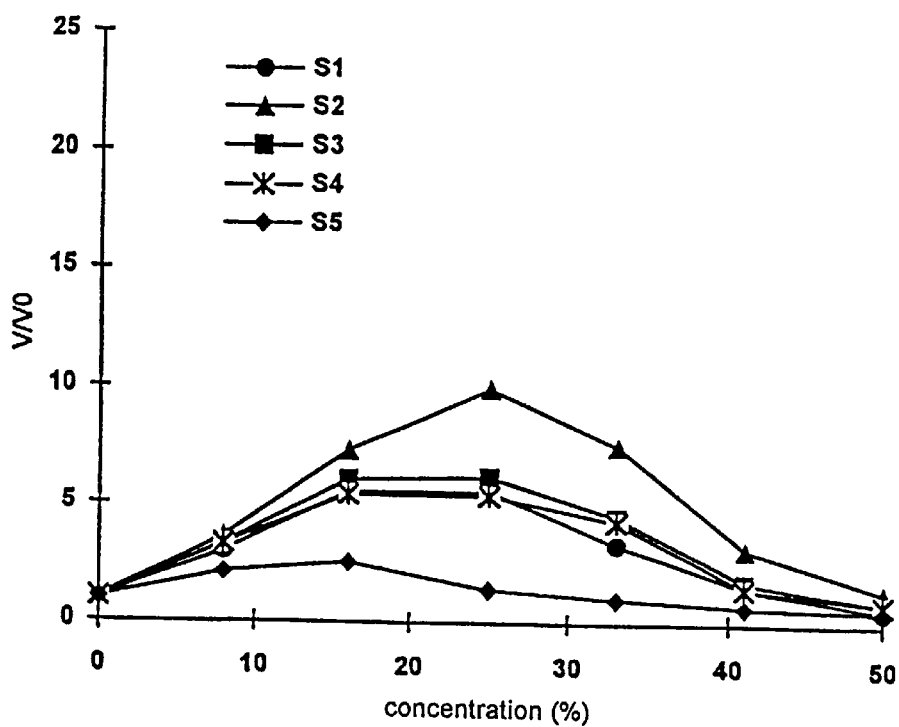
FIG. 2b shows the influence of ethanol on the activity of rFIXa. S1=$MeSO_2$-D-HHT-Gly-Arg-pNA; S2=MOC-D-Nle-Gly-Arg-pNA; S3=$MeSO_2$-D-CHG-Gly-Arg-pNA; S4=$MeSO_2$-D-CHA-Gly-Arg-pNA; S5=$MeSO_2$-D-CHA-Gly-Arg-AMC; rFIXa=0.48 μmol/l; pH=7.4—figure for table 3

The results are summarized in table 3, the results with ethylene glycol are shown in FIG. 2a and the results with ethanol are shown in FIG. 2b.

TABLE 3

| Substrate | $V/V_0$ Additive [%] | | | | | | |
|---|---|---|---|---|---|---|---|
| Additive | 0 | 8 | 16 | 25 | 33 | 41 | 50 |
| MeSO$_2$—D—HHT—Gly—Arg—pNA | | | | | | | |
| ethanol | 1 | 2.99 | 5.52 | 5.57 | 3.35 | 1.48 | 0.60 |
| ethylene glycol | 1 | 2.91 | 6.05 | 10.27 | 12.68 | 9.68 | 3.41 |
| MOC—D—Nle—Gly—Arg—pNA | | | | | | | |
| ethanol | 1 | 3.63 | 7.28 | 9.95 | 7.51 | 3.15 | 1.39 |
| ethylene glycol | 1 | 3.91 | 8.85 | 17.07 | 22.42 | 17.80 | 6.96 |
| MeSO$_2$—D—CHG—Gly—Arg—pNA | | | | | | | |
| ethanol | 1 | 3.33 | 6.02 | 6.16 | 4.50 | 1.74 | 0.87 |
| ethylene glycol | 1 | 5.47 | 13.13 | 19.37 | 23.20 | 17.40 | 5.67 |
| MeSO$_2$—D—CHA—Gly—Arg—pNA | | | | | | | |
| ethanol | 1 | 3.30 | 5.40 | 5.38 | 4.30 | 1.48 | 0.89 |
| ethylene glycol | 1 | 2.84 | 6.26 | 9.34 | 11.18 | 7.54 | 2.56 |
| MeSO$_2$—D—CHA—Gly—Arg—AMC | | | | | | | |
| ethanol | 1 | 2.09 | 2.50 | 1.37 | 1.01 | 0.70 | 0.58 |
| ethylene glycol | 1 | 2.55 | 5.59 | 8.40 | 8.90 | 5.79 | 1.44 |

Result

The stimulation of rFIXa by ethanol and ethylene glycol expressed as the quotient $V/V_0$ is further increased when using the peptide substrates MOC-D-Nle-Gly-Arg-pNA and MeSO$_2$-D-CHG-Gly-Arg-pNA instead of MeSO$_2$-D-HHT-Gly-Arg-pNA. Above 25% ethylene glycol the quotient $V/V_0$ is 1.5–2-fold higher than with the substrate MeSO$_2$-D-HHT-Gly-Arg-pNA.

The cleavage of the fluorogenic substrate MeSO$_2$-D-CHA-Gly-Arg-AMC is also stimulated by alcohols in a comparable manner. The cleavage of tripeptides with the sequence MeSO$_2$-D-CHA-Gly-Arg and C-terminal AMC or pNA is increased by 9 and 11 times respectively by ethylene glycol (33%). Due to the higher sensitivity, much less (1/10) rFIXa must be used to cleave the fluorogenic substrate MeSO$_2$-D-CHA-Gly-Arg-AMC.

EXAMPLE 12

Influence of Ethylene Glycol on the Kinetics of Cleavage of the Chromogenic Peptide Substrates MeSO$_2$-D-HHT-Gly-Arg-pNA, MOC-D-Nle-Gly-Arg-pNA and MeSO$_2$-D-CHG-Gly-Arg-pNA by Recombinant Human FIXa and Native FIXa Test Mixture (Concentration in the Test)

42 mmol/l Tris-HCl, pH 7.4
82 mmol/l NaCl
4.1 mmol/l CaCl$_2$
0–50% ethylene glycol
MeSO$_2$-D-HHT-Gly-Arg-pNA (0.102–1.02 mmol/l)
0.48 μmol/l rFIXa (human)

or

MeSO$_2$-D-HHT-Gly-Arg-pNA (0.102–1.02 mmol/l)
0.29 μmol/l native FIXa (human)

or

MOC-D-Nle-Gly-Arg-pNA (0.102–1.02 mmol/l)
0.48 μmol/l rFIXa (human)

or

MeSO$_2$-D-CHG-Gly-Arg-pNA (0.102–1.02 mmol/l)
0.28 μmol/l rFIXa (human)

The kinetic constants ($K_{cat}/K_m$) were determined graphically according to Lineweaver Burk ($K_m$ and $K_{cat}$ cannot be determined separately since the straight lines go through the origin).

TABLE 4a

Substrate: MeSO$_2$—D—HHT—Gly—Arg—pNA

| | | | $k_{kat}/K_m$ [l/mmol*s] ethylene glycol concentration [%] | | | | |
|---|---|---|---|---|---|---|---|
| Enzyme | 0 | 8 | 16 | 25 | 33 | 41 | 50 |
| rFIXa | n.l. | 0.348 | 0.515 | 1.018 | 1.018 | 0.692 | 0.172 |
| native FIXa | n.l | 0.299 | 0.737 | 1.169 | 1.395 | 0.922 | 0.390 |

TABLE 4b

Different substrates, rFIXa

| | | | $k_{kat}/K_m$ [l/mmol*s] ethylene glycol concentration [%] | | | | |
|---|---|---|---|---|---|---|---|
| Substrate | 0 | 8 | 16 | 25 | 33 | 41 | 50 |
| MeSO$_2$—D—HHT—Gly—Arg—pNA | n.l. | 0.348 | 0.515 | 1.018 | 1.018 | 0.692 | 0.172 |
| MOC—D—Nle—Gly—Arg—pNA | n.l. | n.l. | 0.326 | 0.565 | 0.552 | 0.360 | 0.148 |
| MeSO$_2$—D—CHG—Gly—Arg—pNA | n.l. | 0.637 | 1.974 | 2.880 | 3.480 | 1.929 | 0.576 | n.l. = nol-linear

Result

The stimulation of the cleavage of chromogenic peptide substrates catalysed by recombinant or native human FIXa is also found for the kinetic constants, $K_{cat}/K_m$ increases up to an ethylene glycol concentration of 33%. In the case of the substrate MeSO$_2$-D-CHG-Gly-Arg-pNA the highest catalytic activity i.e. the highest value for $K_{cat}/K_m$ is found at 33% ethylene glycol. In the case of the uninfluenced reaction the plot is not linear and no constant can be determined.

Figure 3A:
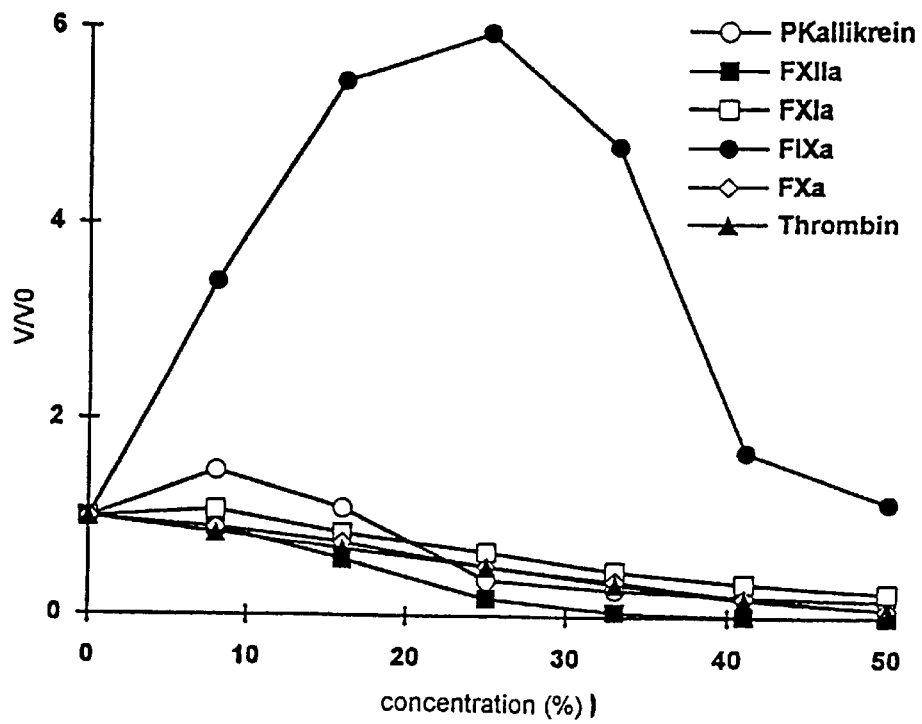
FIG. 3a shows the influence of ethanol on the activity of P-kallikrein, FXIIa, FXIa, FIXa, FXa and thrombin (pH 7.4; 1.02 mmol/l $MeSO_2$-D-HHT-Gly-Arg-pNA)—figure for table 5.
Figure 3B:
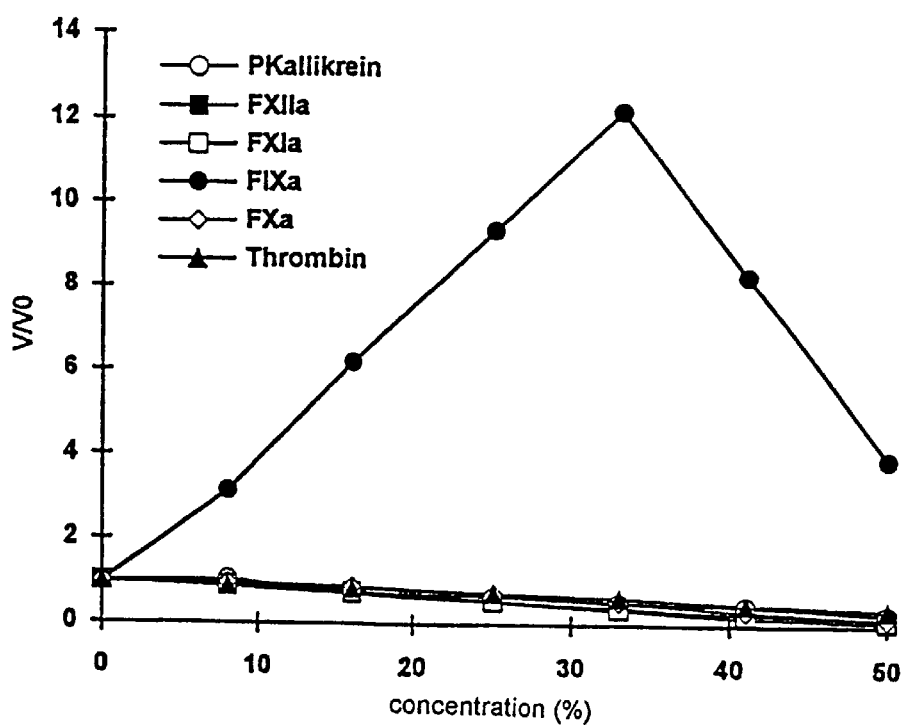
FIG. 3b shows the influence of ethylene glycol on the activity of P-kallikrein, FXIIa, FXIa, FIXa, FXa and thrombin (pH 7.4; 1.02 mmol/l $MeSO_2$-D-HHT-Gly-Arg-pNA)—figure for table 6.

EXAMPLE 13
Influence of Ethanol and Ethylene Glycol on the Activity of FIXa in Comparison with Plasma Kallikrein, FXIIa, FXIa, FXa and Thrombin FIXa Test Mixture (Concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.14 μmol/l native FIXa (human)
 0–50% ethanol or ethylene glycol
Plasma Kallikrein Test Mixture (Concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.0176 U/ml plasma kallikrein (human)
 0–50% ethanol or ethylene glycol
FXIIa Test Mixture (Concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.0045 U/ml FXIIa (human)
 0–50% ethanol or ethylene glycol
FXIa Test Mixture (Concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.0012 μmol/l FXIa (human)
 0–50% ethanol or ethylene glycol
FXa Test Mixture (concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.088 μmol/l FXa (bovine)
 0–50% ethanol or ethylene glycol
Thrombin Test Mixture (Concentration in the Test)
 42 mmol/l Tris-HCl, pH 7.4
 82 mmol/l NaCl
 4.1 mmol/l CaCl$_2$
 1.02 mmol/l MeSO$_2$-D-HHT-Gly-Arg-pNA
 0.045 μmol/l thrombin (bovine)
 0–50% ethanol or ethylene glycol The results are summarized in tables 5 and 6, the effect of ethanol is shown in FIG. 3a and the effect of ethylene glycol is shown in FIG. 3b.

TABLE 5

| | $V/V_0$ ethanol concentration [%] | | | | | | |
|---|---|---|---|---|---|---|---|
| Protease | 0 | 8 | 16 | 25 | 33 | 41 | 50 |
| PKallikrein | 1 | 1.48 | 1.10 | 0.377 | 0.280 | 0.215 | 0.174 |
| FXIIa | 1 | 0.904 | 0.579 | 0.187 | 0.051 | 0.009 | 0 |
| FXIa | 1 | 1.08 | 0.845 | 0.657 | 0.469 | 0.353 | 0.258 |
| FIXa | 1 | 3.40 | 5.46 | 5.96 | 4.82 | 1.69 | 1.17 |
| FXa | 1 | 0.899 | 0.752 | 0.510 | 0.377 | 0.203 | 0.086 |
| thrombin | 1 | 0.846 | 0.685 | 0.507 | 0.343 | 0.184 | 0.087 |

TABLE 6

| | $V/V_0$ ethylene glycol concentration [%] | | | | | | |
|---|---|---|---|---|---|---|---|
| Protease | 0 | 8 | 16 | 25 | 33 | 41 | 50 |
| PKallikrein | 1 | 1.05 | 0.763 | 0.676 | 0.536 | 0.478 | 0.290 |
| F XIIa | 1 | 0.892 | 0.729 | 0.551 | 0.355 | 0.187 | 0.103 |
| FXIa | 1 | 0.922 | 0.790 | 0.569 | 0.422 | 0.275 | 0.165 |
| FIXa | 1 | 3.13 | 6.19 | 9.36 | 12.21 | 8.29 | 3.92 |
| FXa | 1 | 0.973 | 0.902 | 0.741 | 0.558 | 0.347 | 0.191 |
| thrombin | 1 | 0.924 | 0.862 | 0.763 | 0.653 | 0.508 | 0.395 |

Result

Among the coagulation factors of the intrinsic activation path—plasma kallikrein, FXIIa, FXIa, FIXa, FXa and thrombin—only FIXa is activated by ethanol and ethylene glycol. A slight activation is observed in the presence of 10–20% ethanol in the case of plasma kallikrein.

EXAMPLE 14
Influence of the pH on the Activity of rFIXa and Native FIXa in the Presence of Ethylene Glycol Test Mixture (Concentration in the Test)
 42 mmol/l Tris-HCl, pH 7.0–10.0
 82 mmol/l NaCl
 4.1 mmol/l CaCl$_2$
 1.02 mmol/l MeSO$_2$-D-HHT-Gly-Arg-pNA, MOC-D-Nle-Gly-Arg-pNA or MeSO$_2$-D-CHG-Gly-Arg-pNA 25% ethylene glycol
0.28 µmol/l rFIXa (human)
or
0.14 µmol/l native FIXa (human)
The results are shown in Table 7a–d.

TABLE 7a

Substrate: MeSO$_2$—D—HHT—Gly—Arg-pNA, rFIXa (human)

| Additive/ | mA/min | | | | | | | | |
|---|---|---|---|---|---|---|---|---|---|
| pH | 7.0 | 7.5 | 8.0 | 8.25 | 8.5 | 8.75 | 9.0 | 9.5 | 10.0 |
| without | 6.5 | 10.7 | 16.0 | 17.0 | 16.3 | 16.3 | 16.0 | 12.9 | 10.4 |
| ethylene glycol [25%] | 56.5 | 124.5 | 173.6 | 176.0 | 182.1 | 170.7 | 164.1 | 112.0 | 110.1 |

TABLE 7b

Substrate: MeSO$_2$—D—HHT—Gly—Arg—pNA, native FIXa (human)

| Additive/ | mA/min | | | | | | | | |
|---|---|---|---|---|---|---|---|---|---|
| pH | 7.0 | 7.5 | 8.0 | 8.25 | 8.5 | 8.75 | 9.0 | 9.5 | 10.0 |
| without | 3.3 | 6.8 | 10.0 | 10.5 | 10.3 | 9.9 | 9.3 | 7.4 | 6.2 |
| ethylene glycol [25%] | 23.7 | 63.0 | 101.0 | 106.7 | 115.4 | 110.9 | 105.6 | 100.6 | 77.2 |

TABLE 7c

Substrate: MOC—D—Nle—Gly—Arg—pNA, rFIXa (human)

| Additive/ | mA/min | | | | | | | | |
|---|---|---|---|---|---|---|---|---|---|
| pH | 7.0 | 7.5 | 8.0 | 8.25 | 8.5 | 8.75 | 9.0 | 9.5 | 10.0 |
| without | 3.1 | 5.2 | 6.8 | 7.3 | 7.9 | 7.1 | 7.1 | 7.0 | 5.2 |
| ethylene glycol [25%] | 31.5 | 70.1 | 99.7 | 102.7 | 104.3 | 101.6 | 97.3 | 70.7 | 68.3 |

TABLE 7d

Substrate: MeSO$_2$—D—CHG—Gly—Arg—pNA, rFIXa (human)

| Additive/ | mA/min | | | | | | | | |
|---|---|---|---|---|---|---|---|---|---|
| pH | 7.0 | 7.5 | 8.0 | 8.25 | 8.5 | 8.75 | 9.0 | 9.5 | 10.0 |
| without | 6.5 | 11.3 | 18.1 | 18.8 | 19.6 | 20.3 | 18.4 | 14.8 | 11.3 |
| ethylene glycol [25%] | 154.7 | 289.8 | 372.4 | 382.2 | 389.8 | 395.6 | 373.3 | 255.6 | 244.5 |

Result

The pH dependency of the catalytic activity of rFIXa is not altered by alcohols as demonstrated with ethylene glycol as an example. Thus the cleavage rates increased in the same ratio between pH 7.0 and 10.0 in the presence of 25% ethylene glycol. The cleavage rates in the presence of the substrate MeSO$_2$-D-HHT-Gly-Arg-pNA increased 10-fold, in the case of MOC-D-Nle-Gly-Arg-pNA and MeSO$_2$-D-CHG-Gly-Arg-pNA the increases were 14-fold and 20-fold respectively. The optimal pH range is between pH 8.25 and 8.75. The substrate MeSO$_2$-D-CHG-Gly-Arg-pNA is cleaved most effectively.

EXAMPLE 15

Screening Test for FIXa Inhibitors

Specific FIXa inhibitors can be identified by the inhibition of FIXa activity. For this purpose the FIXa activity is determined with a substrate of the R-D-Xxx-Gly-Arg-pNA type (Xxx=hydrophobic amino acid) in the absence and presence of the substance to be tested or of a substance mixture and the percentage inhibition is calculated from the quotients. The inhibition constant $K_i$ is determined from the inhibition kinetics. The measurement signal is amplified by the presence of high concentrations of certain alcohols (preferably ethylene glycol).

Test Principle

FIXa

R-D-Xxx-Gly-Arg-pNA→R-D-Xxx-Gly-Arg+pNA measurement signal: pNA

FIXa substrates: MeSO$_2$-D-HHT-Gly-Arg-pNA (Pefachrom tPA) MOC-D-Nle-Gly-Arg-pNA (Chromozym X) MeSO$_2$-D-CHG-Gly-Arg-pNA FIXa: recombinantly produced rFIXa (human)

Test mixture

200 µl buffer (100 mmol/l Tris-HCl, 100 mmol/l NaCl, 5 mmol/l CaCl$_2$, 20–40% alcohol, pH 7–9) the buffer contains the inhibitor at various concentrations +25 µl peptide substrate +20 µl rFIXa (human)

The test mixture was incubated at RT in a microtitre plate and the change in absorbance (ΔA/min) at 405 nm was determined with an ELISA reader. The reaction can also be terminated after 5–10 min by stopping with acetic acid (25 µl, 50%), the absorbance is determined at 405 nm against a reagent blank.

EXAMPLE 16

Influence of Known Protease Inhibitors on the Activity of rFIXa Using Different pHs, Alcohols and Alcohol Concentrations Test Mixture (Concentration in the Test)

42 mmol/l Tris-HCl, pH 7.4 or 8.5

82 mmol/l NaCl 4.1 mmol/l CaCl$_2$ substrate MeSO$_2$-D-CHG-Gly-Arg-pNA (1.02 mmol/l)

0.028–0.57 µmol/l rFIXa (human)

4.1% ethanol or 33% ethylene glycol inhibitor at stepped concentrations (4.1–163 µmol/l)

Known synthetic inhibitors of the 3-amidinophenylalanine type were used as inhibitors (Sturzebecher et al, J. Enzyme. Inhibition 9 (1995) 87 and WO 92/08709) (1991)). The inhibitory effect was examined at a low and at a high alcohol concentration as an example.

TABLE 8a

Inhibition of the activity of factor IXa (in %) by the inhibitor Nα-(2,4,6-triisopropylbenzenesulfonyl)-3-amidino-(D,L)-phenylalanine-isonipecotic acid [TIPPS-(3-Am)Phe-iNip-OH]

| Conditions | Inhibitor concentration [μmol/l] | | | | | |
|---|---|---|---|---|---|---|
| | 4.1 | 8.2 | 16.3 | 40.8 | 81.6 | 163 |
| pH 7.4; 4.1% ethanol 0.57 μmol/l rFIXa | 89.5 | 87.6 | 76.2 | 55.8 | 36.3 | 23.8 |
| pH 8.5; 4.1% ethanol 0.28 μmol/l rFIXa | 90.6 | 85.2 | 74.8 | 55.2 | 35.3 | 20.8 |
| pH 7.4; 33% ethylene glycol 0.057 μmol/l rFIXa | 86.9 | 79.4 | 61.7 | 38.9 | 21.2 | 15.0 |
| pH 8.5; 33% ethylene glycol 0.028 μmol/l rFIXa | 85.6 | 72.8 | 58.0 | 33.6 | 20.7 | 15.8 |

TABLE 8b

Inhibition of the activity of factor IXa (in %) by the inhibitor Nα-(2-naphthylsulfonyl)-3-amidino-(D,L)-phenylalanine-1,2,3,4-tetrahydroisoquinoline-3-carboxylic acid [βNAPS-(3-Am)Phe-TIC-OH]

| Conditions | Inhibitor concentration [μmol/l] | | | | | |
|---|---|---|---|---|---|---|
| | 4.1 | 8.2 | 16.3 | 40.8 | 81.6 | 163 |
| pH 7.4; 4.1% ethanol 0.57 μmol/l rFIXa | 97.2 | 97.2 | 88.2 | 75.4 | 57.0 | 25.7 |
| pH 8.5; 4.1% ethanol 0.28 μmol/l rFIXa | 100 | 96.2 | 86.2 | 77.5 | 63.8 | 48.8 |
| pH 7.4; 33% ethylene glycol 0.057 μmol/l rFIXa | 100 | 100 | 85.4 | 62.6 | 41.0 | 28.9 |
| pH 8.5; 33% ethylene glycol 0.028 μmol/l rFIXa | 100 | 97.9 | 88.4 | 78.4 | 66.0 | 45.4 |

Result

The inhibition of rFIXa by a synthetic inhibitor can be examined at various pHs (pH 7–9) and at various alcohol contents (preferably ethanol or ethylene glycol). For a 50% inhibition of rFIXa $IC_{50}$ values between 20 and 50 μmol/l were found for the inhibitor TIPPS-(3-Am)Phe-iNip-OH and $IC_{50}$ values between 60 and 150 μmol/l were found for the inhibitor βNAPS-(3-Am)Phe-TIC-OH. The inhibitory effect can be detected most sensitively at a high ethylene glycol concentration and pH 8.5. This approach is suitable as a screening method for searching for FIXa inhibitors since extremely low amounts of rFIXa are required and the high alcohol concentrations facilitate the dissolution of the substances to be tested.

EXAMPLE 17

Determination of the Dissociation Constant $K_i$ According to the Method of DIXON Test Mixture (Concentration in the Test)

42 mmol/l Tris-HCl, pH 8.5
82 mmol/l NaCl
4.1 mmol/l $CaCl_2$
33% ethylene glycol
inhibitor in stepped concentrations (0, 20.4 and 40.8 μmol/l)
$MeSO_2$-D-HHT-Gly-Arg-pNA (1.02, 0.51 and 0.25 mmol/l)
0.14 μmol/l rFIXa (human)

or $MeSO_2$-D-HHT-Gly-Arg-pNA (1.02, 0.51 and 0.25 mmol/l)
0.07 μmol/l native FIXa (human)

or $MeSO_2$-D-CHG-Gly-Arg-pNA (1.02, 0.51 and 0.25 mmol/l)
0.14 μmol/l rFIXa (human)

TIPPS-(3-Am)Phe-iNip-OH was used as the inhibitor and the inhibitory effect was determined as an example for two substrates under optimal conditions (pH 8.5, 33% ethylene glycol).

TABLE 9a

Substrate: $MeSO_2$-D-HHT-Gly-Arg-pNA, 0.14 μmol/l rFIXa

| Substrate concentration | Inhibitor concentration [μmol/l] 1/V [min/mA] | | |
|---|---|---|---|
| | 0 | 20.4 | 40.8 |
| 1.02 μmol/l | 9.5 | 16.6 | 31.2 |
| 0.51 μmol/l | 20.9 | 43.5 | 90.9 |
| 0.25 μmol/l | 33.2 | 69.4 | 137 |

TABLE 9a

Substrate: $MeSO_2$-D-HHT-Gly-Arg-pNA, 0.07 μmol/l native FIXa

| Substrate concentration | Inhibitor concentration [μmol/l] 1/V [min/mA] | | |
|---|---|---|---|
| | 0 | 20.4 | 40.8 |
| 1.02 μmol/l | 16.4 | 29.5 | 53.2 |
| 0.51 μmol/l | 38.6 | 77.5 | 154 |
| 0.25 μmol/l | 59.5 | 129 | 255 |

TABLE 9c

Substrate: $MeSO_2$-D-CHG-Gly-Arg-pNA, 0.057 μmol/l rFIXa

| Substrate concentration | Inhibitor concentration [μmol/l] 1/V [min/mA] | | |
|---|---|---|---|
| | 0 | 20.4 | 40.8 |
| 1.02 μmol/l | 15.5 | 23.8 | 44.6 |
| 0.51 μmol/l | 28.7 | 55.6 | 109 |
| 0.25 μmol/l | 43.1 | 78.1 | 153 |

Result

The determination of the dissociation constant $K_i$ according to DIXON for the inhibition of recombinant or native human FIXa by TIPPS-(3-Am)Phe-iNip-OH was carried out at pH 8.5 and at an optimal ethylene glycol concentration (33%). Comparable $K_i$ values (12 and 9 μmol/l respectively) were determined graphically for the inhibition of recombinant and native FIXa using the values summarized in tables 9a and 9b. Comparable Ki values (12 and 16 μmol/l respectively) also resulted when using the substrates $MeSO_2$-D-HHT-Gly-Arg-pNA and $MeSO_2$-D-CHG-Arg-pNA for the inhibition of rFIXa. The selected mixture with a high ethylene glycol concentration is especially suitable for determining inhibition constants since low rFIXa concentrations are required. High alcohol concentrations in addition facilitate the dissolution of the substances to be tested.

List of references

Bang, N. U., et al, EP 0 191 606
Bergmeyer, H. U. (ed.): Methods of Enzymatic Analysis, Vol. V, chapter 3, 3rd ed., Academic Press, New York (1983)
Bharadwaj, D., et al., J. Biol. Chem. 270, 6537–6542 (1995)
Blow, D. M., Acc. Chem. Res. 9, 145–152 (1976)
Brinkmann, U., et al., Gene 85, 109114 (1989)
Davie, E. W., et al., Biochem. 30, 10363–10379 (1991)
Esmon, C. T., Prothrombin activation, doctoral dissertation, Washington University, St. Louis, Mo. (1973)
European Patent Application No. 96 109 288.9
European Patent Application No. 96 110 959.2
European Patent EP-B 0 034 122
Fujikawa, K., et al., Biochem. 11, 4892–4898 (1972)
Furie, B.; Furie, B. C., Cell 53, 505–518 (1988)
Grodberg, J.; Dunn, J. J., J. Bacteriol. 170, 1245–1253 (1988)
Hagen, F. S., et al, EP 0 200 421
Hertzberg, M. S., et al., J. Biol. Chem. 267, 14759–14766 (1992)
Holly, R. D.; Foster, D. C., WO 93/13208
Hopfner, K.-P.; Kopetzki, E., European Patent Application No. 96 110 959.2
Kopetzki, E., et al., WO 93/09144
Laemmli, U. K., Nature 227, 680–685 (1970) Lin, S.-W., et al., J. Biol. Chem. 265, 144–150 (1990)
McGraw, R. A., et al., Proc. Natl. Acad. Sci. USA 82, 2847–2851 (1985)
Medved, L. V., et al., J. Biol. Chem. 270, 13652–13659 (1995)
Nicolaisen, E. M., et al., WO 88/10295
Pedersen, A. H., et al., Biochem. 28, 9391–9336 (1989)
Polgar, L., : Structure and function of serine proteases. In: Mechanisms of protein action. Boca Raton, Fla., CRC Press, chapter 3 (1989)
Rezaie, A. R., et al., J. Biol. Chem. 268, 8176–8180 (1993)
Rezaie, A. R.; Esmon, C. T., J. Biol. Chem. 269; 21495–21499 (1994)
Sambrook, J.; Fritsch, E. F.; Maniatis,T.: Molecular cloning: A laboratory manual. Cold Spring Harbor Press, Cold Spring Harbor, N.Y., (1989)
Sheehan, J. P., et al., J. Biol. Chem. 268, 3639–3645 (1993)
Svendsen, L. G., European Patent EP-B 0 034 122
Thogersen, H. C., et al., WO 94/18227
Stürzebecher, et al., J. Enzym. Inhibition 9 (1995) 87
Stürzebecher, et al., WO 92/08709, 1991
Van Dam-Mieras, M. C. E., et al.: Blood coagulation factors II, V, VII, VIII, IX, X and XI: Determination with synthetic substrates. In: Bergmeyer, H. U. (ed.): Methods of Enzymatic Analysis, Vol. V, Enzymes 3: Peptidases, Proteinases and Their Inhibitors, page 365–394, 3rd ed., Academic Press, New York (1983)
Wolf, D. L., et al., J. Biol. Chem. 266, 13726–13730 (1991)
Yee, J., et al., J. Biol. Chem. 269, 17965–17970 (1994)
Zhong, D. G., et al., Proc. Natl. Acad. Sci. USA 91, 3574–3578 (1994)

I claim:

1. A method for determining the presence of factor IXa activity in a sample solution, which comprises:
   (a) adding to the sample solution a known amount of a measurable factor IXa substrate and an alcohol that is homogeneously miscible with the sample solution; and
   (b) determining if the factor IXa substrate has been cleaved, the cleavage of the factor IXa substrate indicating the presence of factor IXa activity in the sample solution.

2. The method according to claim 1, wherein the factor IXa substrate is a tripeptide having a hydrophobic D-amino acid at the N-terminus.

3. The method according to claim 2, wherein the factor IXa substrate that is added is a cyclohexyl-substituted-hydrophobic D-amino acid.

4. The method according to claim 1, wherein the alcohol is selected from the group consisting of methanol, ethanol, n-propanol, i-propanol, t-butanol, glycerol, and ethylene glycol.

5. The method according to claim 4, wherein the alcohol is selected from the group consisting of methanol, ethanol, and ethylene glycol.

6. The method according to claim 5, wherein the alcohol is ethylene glycol.

7. The method according to claim 5, wherein the methanol, ethanol, or ethylene glycol is added in the range of 15% to 40% by volume of the sample solution.

8. A method for determining the amount of factor IXa activity in a sample solution, which comprises:
   (a) adding to the sample solution a known amount of a measurable factor IXa substrate and an alcohol that is homogeneously miscible with the sample solution;
   (b) determining the amount of the factor IXa substrate that has been cleaved; and
   (c) correlating the amount of the factor IXa substrate that has been cleaved with a known activity of factor IXa, thereby determining the amount of factor IXa activity in the sample solution.

9. The method according to claim 8, wherein the factor IXa substrate is a tripeptide having a hydrophobic D-amino acid at the N-terminus.

10. The method according to claim 9, wherein the factor IXa substrate that is added is a cyclohexyl-substituted-hydrophobic D-amino acid.

11. The method according to claim 8, wherein the alcohol is selected from the group consisting of methanol, ethanol, n-propanol, i-propanol, t-butanol, glycerol, and ethylene glycol.

12. The method according to claim 11, wherein the alcohol is selected from the group consisting of methanol, ethanol, and ethylene glycol.

13. The method according to claim 12, wherein the alcohol is ethylene glycol.

14. The method according to claim 12, wherein the methanol, ethanol, or ethylene glycol is added in the range of 15% to 40% by volume of the sample solution.

15. A method for increasing the factor IXa activity of a substance having factor IXa activity, which comprises:
   (a) adding a homogeneously miscible alcohol to a sample solution in an amount effective to increase factor IXa activity; and
   (b) reacting the substance having factor IXa activity with a factor IXa substrate in the sample solution containing the homogeneously miscible alcohol; wherein the alcohol is selected from the group consisting of methanol, ethanol, n-propanol, i-propanol, t-butanol, glycerol, and ethylene glycol.

16. The method according to claim 15, wherein the factor IXa substrate is a tripeptide having a hydrophobic D-amino acid at the N-terminus.

17. The method according to claim 16, wherein the factor IXa substrate is a cyclohexyl-substituted-hydrophobic D-amino acid.

18. The method according to claim 15, wherein the homogeneously miscible alcohol is selected from the group consisting of methanol, ethanol, and ethylene glycol.

19. The method according to claim 18, wherein the alcohol is ethylene glycol.

20. The method according to claim 18, wherein the methanol, ethanol, or ethylene glycol is in the range of 15% to 40% by volume of the sample solution.

21. A method for determining the ability of a test substance to modulate factor IXa activity in a solution, which comprises:
   (a) providing a solution containing a substance having factor IXa activity and a test substance;
   (b) adding a factor IXa substrate to the solution in the presence of an alcohol that is homogeneously miscible with the solution;
   (c) measuring the factor IXa activity in the solution of step (b);
   (d) comparing the factor IXa activity in the solution comprising the test substance with the factor IXa activity of another solution that is identical except for the absence of the test substance, the difference in activity representing the amount of factor IXa modulating activity attributable to the test substance.

22. The method according to claim 21, wherein the factor IXa substrate is a tripeptide having a hydrophobic D-amino acid at the N-terminus.

23. The method according to claim 22, wherein the factor IXa substrate is a cyclohexyl-substituted-hydrophobic D-amino acid.

24. The method according to claim 21, wherein the alcohol is selected from the group consisting of methanol, ethanol, n-propanol, i-propanol, t-butanol, glycerol, and ethylene glycol.

25. The method according to claim 24, wherein the alcohol is selected from the group consisting of methanol, ethanol, and ethylene glycol.

26. The method according to claim 25, wherein the alcohol is ethylene glycol.

27. The method according to claim 25, wherein the methanol, ethanol, or ethylene glycol is added in the range of 15% to 40% by volume of the solution.

28. A reagent which comprises a chromogenic factor IXa substrate that is cleavable by factor IXa activity, an alcohol that is homogeneously miscible with water, and a buffer wherein the reagent has a pH in the range of pH 7 to 10.

29. The reagent according to claim 28, wherein the factor IXa substrate is a tripeptide having a hydrophobic D-amino acid at the N-terminus.

30. The reagent according to claim 28, wherein the factor IXa substrate is a cyclohexyl-substituted-hydrophobic D-amino acid.

31. The reagent according to claim 28, wherein the alcohol is selected from the group consisting of methanol, ethanol, n-propanol, i-propanol, t-butanol, glycerol, and ethylene glycol.

32. The reagent according to claim 31, wherein the alcohol is selected from the group consisting of methanol, ethanol, and ethylene glycol.

33. The reagent according to claim 32, wherein the alcohol is ethylene glycol.

* * * * *